United States Patent
McCleary et al.

(10) Patent No.: US 10,987,496 B2
(45) Date of Patent: Apr. 27, 2021

(54) MEDICAL BALLOON

(71) Applicant: BOSTON SCIENTIFIC SCIMED, INC., Maple Grove, MN (US)

(72) Inventors: Kyle Allen McCleary, Coon Rapids, MN (US); Daniel James Horn, Shoreview, MN (US); Jeffrey S. Lindquist, Maple Grove, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 198 days.

(21) Appl. No.: 15/962,432

(22) Filed: Apr. 25, 2018

(65) Prior Publication Data

US 2018/0304054 A1 Oct. 25, 2018

Related U.S. Application Data

(60) Provisional application No. 62/489,973, filed on Apr. 25, 2017.

(51) Int. Cl.
| | | |
|---|---|---|
| *A61M 25/10* | (2013.01) | |
| *A61L 29/06* | (2006.01) | |
| *A61F 2/958* | (2013.01) | |
| *A61L 29/14* | (2006.01) | |
| *A61L 29/08* | (2006.01) | |

(52) U.S. Cl.
CPC ........... *A61M 25/104* (2013.01); *A61F 2/958* (2013.01); *A61L 29/06* (2013.01); *A61L 29/085* (2013.01); *A61L 29/14* (2013.01); *A61M 25/1029* (2013.01); *A61M 2025/1031* (2013.01); *A61M 2025/1075* (2013.01)

(58) Field of Classification Search
CPC ....... A61M 25/104; A61F 2/958; A61L 29/06; A61L 29/085; A61L 29/14
USPC ..................................................... 604/103.06
See application file for complete search history.

(56) References Cited

U.S. PATENT DOCUMENTS

| | | |
|---|---|---|
| 3,023,982 A | 3/1962 | Huch |
| 4,327,736 A | 5/1982 | Inoue |
| 4,490,421 A | 12/1984 | Levy |
| (Continued) | | |

FOREIGN PATENT DOCUMENTS

| | | |
|---|---|---|
| EP | 0553960 A1 | 1/1993 |
| EP | 0540858 A1 | 5/1993 |
| (Continued) | | |

OTHER PUBLICATIONS

International Search Report and Written Opinion dated Jun. 28, 2017 for International Application No. PCT/US2017/027032.
(Continued)

*Primary Examiner* — Phillip A Gray
(74) *Attorney, Agent, or Firm* — Seager, Tufte & Wickhem LLP.

(57) ABSTRACT

A composite expandable medical balloon comprising a base balloon, the base balloon comprising a coextrusion, the coextrusion comprising an inner layer formed from an elastomeric polymer and an outer layer formed from a thermoplastic polymer a fiber braid disposed along the base balloon, the fiber braid comprising at least one polymeric fiber disposed over the base balloon, wherein the base balloon is designed to exhibit minimal delamination between the inner layer the outer layer of the base balloon, and methods of making the same.

20 Claims, 8 Drawing Sheets

(56) References Cited

U.S. PATENT DOCUMENTS

| | | |
|---|---|---|
| 4,706,670 A | 11/1987 | Andersen et al. |
| 4,808,465 A | 2/1989 | Vane |
| 4,896,669 A | 1/1990 | Bhate et al. |
| 4,906,244 A | 3/1990 | Pinchuk et al. |
| 4,935,190 A | 6/1990 | Tennerstedt |
| 4,950,239 A | 8/1990 | Gahara et al. |
| 4,963,313 A | 10/1990 | Noddin et al. |
| 5,026,607 A | 6/1991 | Kiezulas |
| 5,096,848 A | 3/1992 | Kawamura |
| 5,135,516 A | 8/1992 | Sahatjian et al. |
| 5,201,706 A | 4/1993 | Noguchi et al. |
| 5,250,069 A | 10/1993 | Nobuyoshi et al. |
| 5,264,260 A | 11/1993 | Saab |
| 5,270,086 A | 12/1993 | Hamlin |
| 5,304,121 A | 4/1994 | Sahatjian |
| 5,304,340 A | 4/1994 | Downey |
| 5,306,246 A | 4/1994 | Sahatjian et al. |
| 5,314,443 A | 5/1994 | Rudnick |
| 5,328,468 A | 7/1994 | Kaneko et al. |
| 5,330,428 A | 7/1994 | Wang et al. |
| 5,330,429 A | 7/1994 | Noguchi et al. |
| 5,344,400 A | 9/1994 | Kaneko et al. |
| 5,403,340 A | 4/1995 | Wang et al. |
| 5,407,623 A | 4/1995 | Zachariades et al. |
| 5,500,180 A | 3/1996 | Anderson et al. |
| 5,503,631 A | 4/1996 | Onishi et al. |
| 5,509,899 A | 9/1996 | Fan et al. |
| 5,556,383 A | 9/1996 | Wang et al. |
| 5,576,072 A | 11/1996 | Hostettler et al. |
| 5,578,374 A | 11/1996 | Dunbar et al. |
| 5,647,848 A | 7/1997 | Jorgensen |
| 5,693,034 A | 12/1997 | Buscemi et al. |
| 5,702,756 A | 12/1997 | McKean et al. |
| 5,714,110 A | 2/1998 | Wang et al. |
| 5,797,877 A | 8/1998 | Hamilton et al. |
| 5,827,289 A | 10/1998 | Reiley et al. |
| 5,833,657 A | 11/1998 | Reinhardt et al. |
| 5,868,708 A | 2/1999 | Hart et al. |
| 5,913,861 A | 6/1999 | Trotta |
| 5,958,582 A | 9/1999 | Dunbar et al. |
| 6,110,483 A | 8/2000 | Whitbourne et al. |
| 6,146,356 A | 11/2000 | Wang et al. |
| 6,156,254 A | 12/2000 | Andrews et al. |
| 6,267,775 B1 | 7/2001 | Clerc et al. |
| 6,270,522 B1 | 8/2001 | Simhambhatla et al. |
| 6,306,144 B1 | 10/2001 | Sydney et al. |
| 6,416,494 B1 | 7/2002 | Wilkins |
| 6,444,324 B1 | 9/2002 | Yang et al. |
| 6,528,150 B2 | 3/2003 | Nazarova et al. |
| 6,572,813 B1 | 6/2003 | Zhang et al. |
| 6,673,053 B2 | 1/2004 | Wang et al. |
| 6,695,809 B1 | 2/2004 | Lee |
| 6,723,267 B2 | 4/2004 | Simmelink et al. |
| 6,746,425 B1 | 6/2004 | Beckham |
| 6,896,892 B2 | 5/2005 | Mount et al. |
| 7,252,650 B1 | 8/2007 | Andrews et al. |
| 7,635,510 B2 | 12/2009 | Horn et al. |
| 2003/0054090 A1 | 3/2003 | Hansen |
| 2003/0083691 A1* | 5/2003 | Wantink ............ A61M 25/0052 606/194 |
| 2003/0106346 A1 | 6/2003 | Matsumoto |
| 2003/0139798 A1 | 7/2003 | Brown et al. |
| 2004/0006359 A1 | 1/2004 | Laguna |
| 2004/0058603 A1 | 3/2004 | Hayes |
| 2004/0082965 A1 | 4/2004 | Beckham |
| 2004/0098120 A1 | 5/2004 | Williams et al. |
| 2004/0109964 A1 | 6/2004 | Beckham |
| 2006/0008606 A1 | 1/2006 | Horn et al. |
| 2007/0106216 A1 | 5/2007 | Noddin |
| 2009/0012610 A1 | 1/2009 | Olson et al. |
| 2009/0099517 A1 | 4/2009 | Steadham |
| 2010/0010438 A1 | 1/2010 | Simpson |
| 2011/0046654 A1 | 2/2011 | Kuppurathanam |
| 2012/0215165 A1 | 8/2012 | Lee et al. |
| 2012/0277783 A1 | 11/2012 | Cummins et al. |
| 2012/0296363 A1 | 11/2012 | Davies, Jr. et al. |
| 2013/0048200 A1 | 2/2013 | Pepper et al. |
| 2013/0131709 A1 | 5/2013 | Davies, Jr. et al. |
| 2013/0255866 A1 | 10/2013 | Beckham |
| 2014/0166152 A1 | 6/2014 | Graves et al. |
| 2014/0166193 A1 | 6/2014 | Pepper et al. |
| 2014/0182738 A1 | 7/2014 | Simpson |
| 2014/0243874 A1 | 8/2014 | Pepper et al. |
| 2015/0081006 A1 | 3/2015 | Chuter et al. |
| 2015/0374958 A1 | 12/2015 | Khieu et al. |
| 2016/0136397 A1 | 5/2016 | Konstantino et al. |
| 2016/0151611 A1* | 6/2016 | Pepper ............... A61L 29/085 604/103.12 |
| 2017/0043119 A1 | 2/2017 | Kubo et al. |
| 2017/0291014 A1 | 10/2017 | Royer et al. |
| 2017/0354802 A1* | 12/2017 | Krautkremer ......... A61M 25/10 |

FOREIGN PATENT DOCUMENTS

| | | |
|---|---|---|
| EP | 1388346 A1 | 2/2004 |
| EP | 1189553 B1 | 3/2004 |
| WO | 9803218 A1 | 1/1998 |
| WO | 2004028407 A1 | 4/2004 |
| WO | 2004050140 A2 | 6/2004 |
| WO | 2010051488 A1 | 5/2010 |

OTHER PUBLICATIONS

International Search Report and Written Opinion dated Sep. 4, 2017 for International Application No. PCT/US2017/037347.

International Search Report and Written Opinion for Application No. PCT/US2018/029340, 13 pages, dated Jul. 18, 2018.

* cited by examiner

MEDICAL BALLOON

CROSS REFERENCE TO RELATED APPLICATIONS

This application claims the benefit of U.S. Provisional Patent Application Ser. No. 62/489,973 filed on Apr. 25, 2017, the disclosure of which is incorporated herein by reference.

TECHNICAL FIELD

The present disclosure pertains to medical devices and methods for manufacturing medical devices, for example, medical balloons.

BACKGROUND

Medical balloons can be used to administer a variety of treatments. For example, in an angioplasty procedure, a balloon can be used to widen a constricted bodily vessel, such as an artery, for example, a coronary artery. A balloon can also be used to deliver a tubular member, such as a stent, that is placed in the body to reinforce or to reopen a blocked vessel.

In angioplasty, the balloon can be used to treat a stenosis, or a narrowing of the bodily vessel, by collapsing the balloon and delivering it to a region of the vessel that has been narrowed to such a degree that blood flow is restricted. The balloon can be delivered to a target site by passing the catheter over an emplaced guidewire and advancing the catheter to the site. In some cases, the path to the site can be rather tortuous and/or narrow. Upon reaching the site, the balloon is then expanded, e.g., by injecting a fluid into the interior of the balloon. Expanding the balloon can expand the stenosis radially so that the vessel can permit an acceptable rate of blood flow. After use, the balloon is collapsed and withdrawn.

In stent delivery, the stent is compacted on the balloon and transported to a target site. Upon reaching the site, the balloon can be expanded to deform and to fix the stent at a predetermined position, e.g., in contact with the vessel wall. The balloon can then be collapsed and withdrawn.

BRIEF SUMMARY

This disclosure provides design, material, manufacturing method, and use alternatives for medical devices.

In one aspect, the present disclosure relates to a composite expandable medical balloon, the composite expandable medical balloon comprising a base balloon comprising a coextrusion, the coextrusion comprising an inner layer formed from an elastomeric polymer and an outer layer formed from a thermoplastic polymer, and a fiber braid disposed along the base balloon, the fiber braid comprising at least one polymeric fiber disposed over the base balloon, wherein the base balloon is designed to exhibit minimal delamination between the inner layer and the outer layer of the base balloon.

Alternatively or additionally to any of the embodiments above, the elastomeric polymer is a polyether-block-amide block copolymer.

Alternatively or additionally to any of the embodiments above, the thermoplastic polymer is a thermoplastic polyurethane.

Alternatively or additionally to any of the embodiments above, the at least one polymeric fiber comprises an aromatic polyester liquid crystal polymer fiber.

Alternatively or additionally to any of the embodiments above, the at least one polymeric fiber comprises an aromatic polyamide copolymer fiber.

Alternatively or additionally to any of the embodiments above, the at least one polymeric fiber comprises an ultra high molecular weight polyethylene fiber.

Alternatively or additionally to any of the embodiments above, the composite expandable medical balloon further comprises at least one first layer disposed on the fiber braid, the at least one first layer comprising a thermoplastic polymer.

Alternatively or additionally to any of the embodiments above, the at least one first layer comprises a thermoplastic polyurethane.

Alternatively or additionally to any of the embodiments above, the composite expandable medical balloon further comprises at least one second layer, the at least one second layer comprising a lubricious material, the at least one second layer being an outermost layer.

In another aspect, the present disclosure relates to a composite expandable medical balloon, the composite expandable medical balloon comprising a base balloon, the base balloon is formed from a coextrusion comprising an inner layer of an elastomeric polymer, and an outer layer of a thermoplastic polyurethane and a fiber braid comprising at least one polymeric fiber disposed over the base balloon, wherein the base balloon is designed to exhibit minimal delamination between the inner layer the outer layer of the base balloon.

Alternatively or additionally to any of the embodiments above, the elastomeric polymer is a polyether-block-amide copolymer.

Alternatively or additionally to any of the embodiments above, the composite expandable medical balloon further comprises at least one first layer disposed over the fiber braid, the at least one first layer comprising a thermoplastic polymer.

Alternatively or additionally to any of the embodiments above, the first layer comprises a thermoplastic polyurethane.

Alternatively or additionally to any of the embodiments above, the fiber braid comprises an aromatic liquid crystal polymer.

In another aspect, the present disclosure relates to a method of forming a composite expandable medical balloon, the method comprising coextruding a tubular member, the tubular member comprising an inner layer of an elastomeric polymer and an outer layer of a thermoplastic polymer, radially expanding the tubular member to form a base balloon, and disposing a fiber braid comprising at least one polymeric fiber along the base balloon to form a composite balloon, wherein the base balloon is designed to exhibit minimal delamination between the inner layer and the outer layer of the base balloon.

Alternatively or additionally to any of the embodiments above, the method further comprises plasma treating the composite balloon after disposing the fiber braid along the base balloon.

Alternatively or additionally to any of the embodiments above, the method further comprises disposing a first layer over the fiber braid, the first layer comprising a thermoplastic polymer.

Alternatively or additionally to any of the embodiments above, the elastomeric polymer is a polyether-block-amide.

Alternatively or additionally to any of the embodiments above, the thermoplastic polymer is a thermoplastic polyurethane.

Alternatively or additionally to any of the embodiments above, the at least one polymeric fiber is an aromatic polyester liquid crystal polymer fiber.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
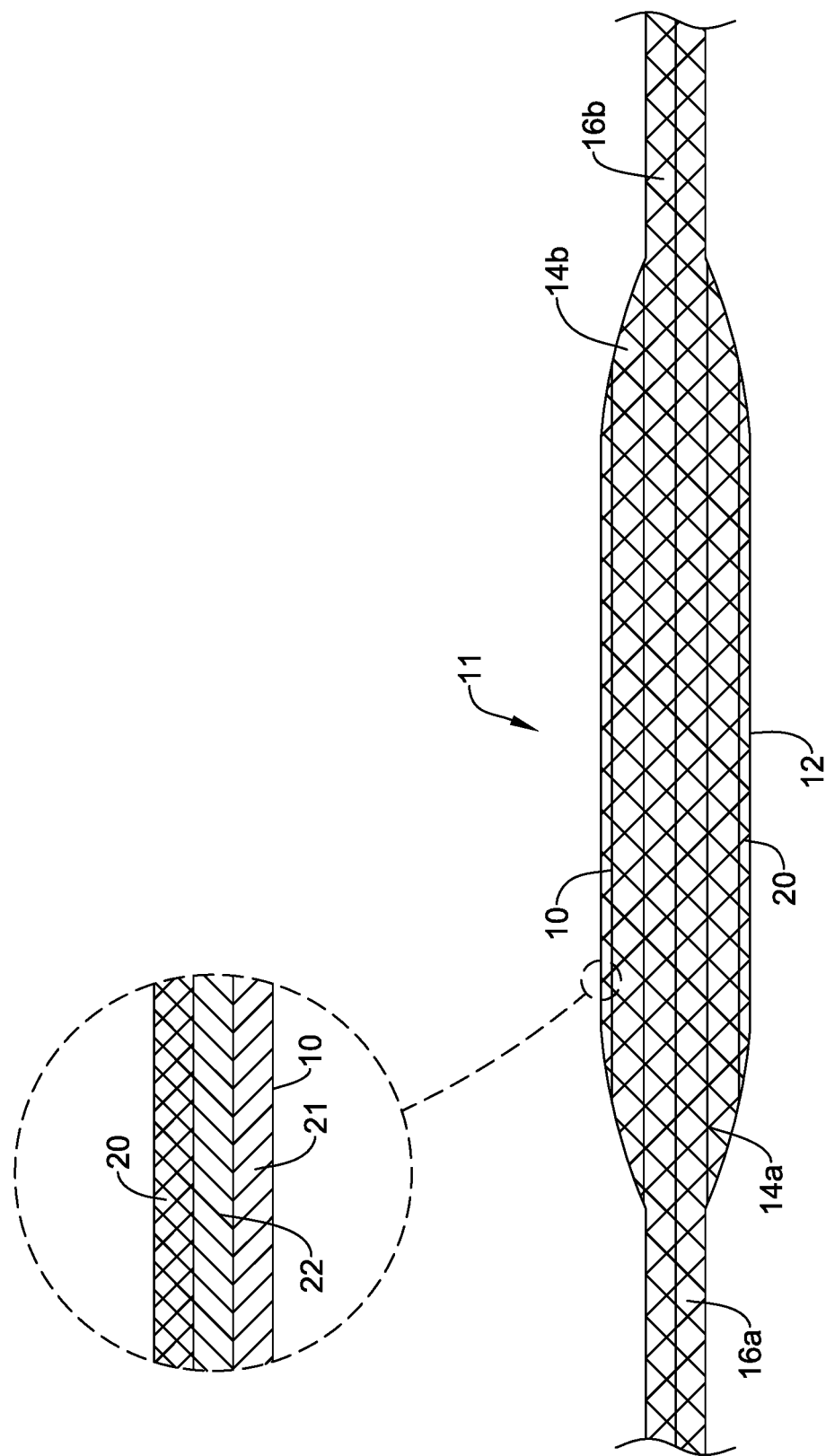
FIG. 1 is a partial cross-sectional side view of an example medical device.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used in connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the disclosure.

The materials that can be used for the various components of the medical devices disclosed herein and the components thereof may include those commonly associated with medical devices, some of which are listed below.

A number of medical balloons may include a balloon or "base balloon" with a reinforcement layer such as a fiber braid disposed thereon. Braided balloon designs may exhibit delamination of the fiber braid from the base balloon as well as delamination from the base balloon of any subsequent layers, for example, other polymer layers disposed between the fiber braid and the base balloon, or other layers disposed over the fiber braid. Delamination can result in pocket formation, increased fluid retention in the pockets that form, and increased withdrawal force from a patient's body lumen after treatment and deflation to remove the balloon from the body lumen.

In some instances, it may be desirable for the fiber braid to be secured to the base balloon in a manner such that the bond between the fiber braid and the base balloon is maintained, for example, by having an additional polymer layer between the fiber braid and the base balloon to increase adhesion of the fiber braid to the base balloon. Better adhesion between the base balloon and a polymeric layer between the base balloon and the fiber braid results in lower amounts of delamination.

The present disclosure relates to a composite expandable medical balloon having a base balloon with at least one elastomeric layer and at least one thermoplastic layer, and a fiber braid disposed thereon that exhibit rated burst strengths of 30 atmospheres or higher, for example 35-70 atmospheres, and that exhibit minimal or no delamination between the at least one elastomeric layer and the at least one thermoplastic layer and/or any layers disposed thereon.

Figure 2:
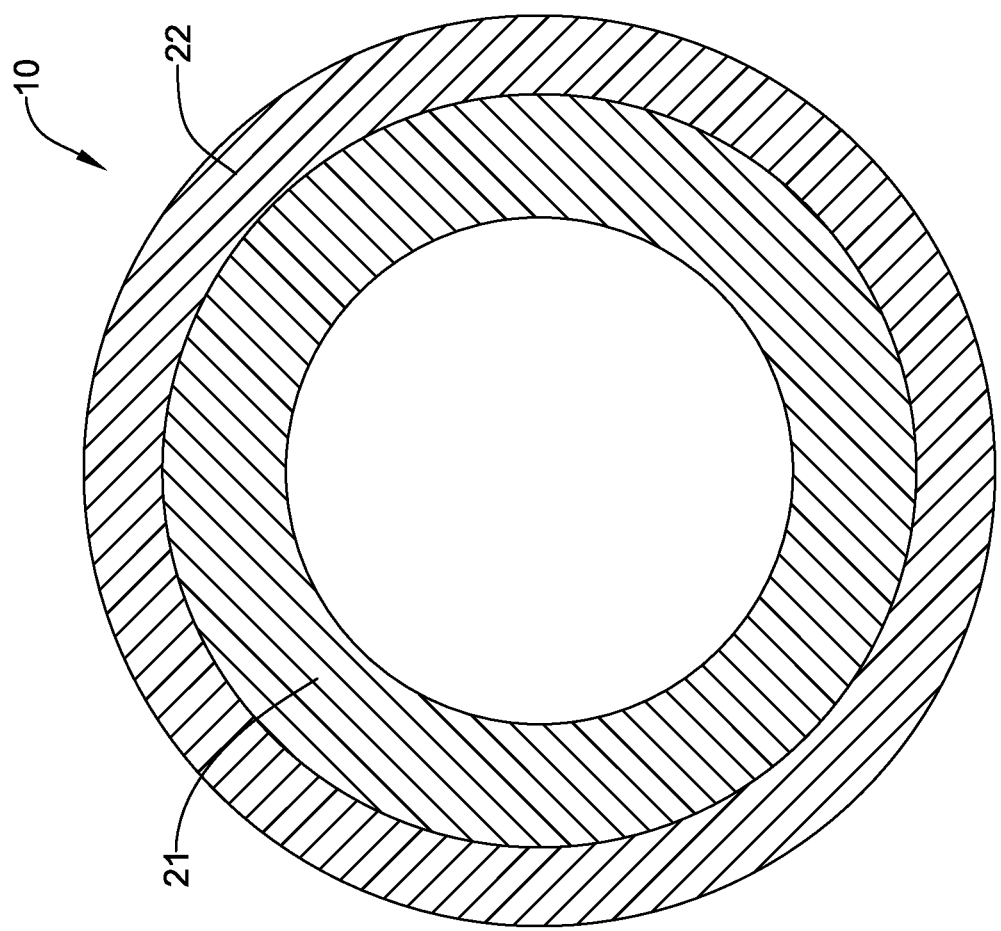
FIG. 2 is a radial cross-section of a portion of an example medical device.

FIG. 1 is a side view of an example medical device. The medical device is, for example, a hybrid or composite balloon 11 including a base balloon 10 formed as a coextrusion that includes a first or inner layer 21 and a second or outer layer 22 as shown in radial cross-section in FIG. 2. In some instances, the inner layer 21 may include an elastomeric polymer. In some of these and in other instances, the outer layer 22 may include a thermoplastic polymer. There may be some mixing of the elastomeric polymer and the thermoplastic polymer at the interface of the inner layer 21 and the outer layer 22. Alternatively, the inner layer 21 and the outer layer 22 may be distinct from one another. The thermoplastic polymer layer 22, is disposed between the elastomeric polymer layer 21 and a fiber braid 20, as shown in the enlarged portion of FIG. 1, for example, to improve adhesion of the fiber braid 20 to the base balloon 10. The base balloon 10, hereinafter, a coextruded base balloon 10, is shown having a body portion 12, a proximal cone portion 14a, a distal cone portion 14b, a proximal waist portion 16a, and a distal waist portion 16b.

The composite balloon 11 may be secured to a tubular member, for example, a catheter shaft (not shown) at the proximal waist portion 16a and the distal waist portions 16b, respectively as discussed in more detail below.

Delamination may be determined by running repeat inflation cycles on the coextruded base balloon 10, wherein the coextruded base balloon 10 is inflated at a rate of 1-1.5 atmosphere/second (14.7-22.05 psi/sec) in a 37° C. water bath to a rated burst pressure of 30 atmospheres (440 psi) and held for 30 seconds, and then deflated and evacuated to a pressure of 0.3 atmospheres (4.4 psi) and held for 10-20 seconds, in up to, or more than, 20 cycles. After each cycle, the balloons can be visually inspected for delamination, fiber movement, cone rounding, or burst. The total time at vacuum between cycles may be about 30-60 seconds, including the observation time. Delamination as used herein refers to adhesive failure of thermoplastic polymer layer 22 from the elastomeric polymer layer 21 and can be determined by visual inspection. The example coextruded base balloons, exhibited no delamination over the course of at least 10 repeat inflation cycles, and exhibited no delamination over the course of at least 20 repeat inflation cycles. In another aspect, the present disclosure relates to a composite expandable medical balloon 11, or full catheter containing the composite expandable medical balloon 11, that exhibits minimal or no delamination between thermoplastic polymer layer 22 and the elastomeric polymer layer 21, of the coextruded base balloon 10, and as a result, minimal or no delamination between any subsequent layers including the fiber braid 20, disposed thereon.

The fiber braid 20 may be disposed along the outer surface of the coextruded base balloon 10. The fiber braid 20 is disposed on and in contact with the thermoplastic polymer layer 22, which increases adhesion of the fiber braid 20 to the elastomeric polymer layer 21. The fiber braid 20 includes windows 18 defined between the fibers of the fiber braid 20 which expose the thermoplastic polymer layer 22, as shown in FIG. 3.

Figure 3:
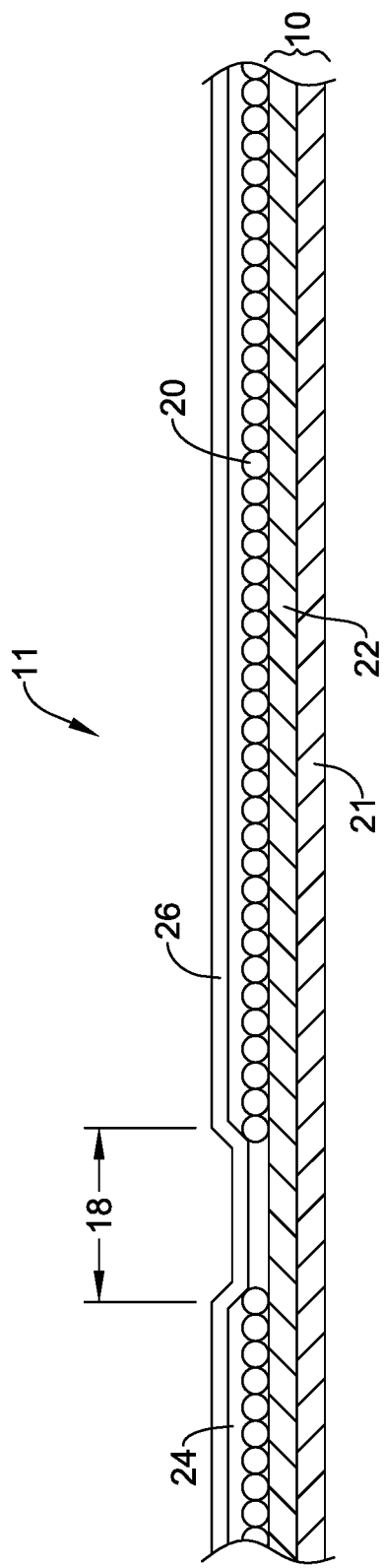
FIG. 3 is a partial cross-section of a portion of an example medical device.

Additional layers may be included, for example, FIG. 3 schematically depicts a cross-sectional view of some of the layers contemplated. For example, some of the layers contemplated for the composite balloon 11 can be seen such as, for example, the coextruded base balloon 10 which is a coextrusion of the elastomeric polymer layer 21 and the thermoplastic polymer layer 22, the fiber braid 20, a layer 24, and optionally an outer layer 26. As discussed above, the composite balloon 11 may incorporate fewer layers or even more layers if desired. For example, the coextruded base balloon 10 and the fiber braid 20; or the coextruded base balloon 10, the fiber braid 20 and the layer 24; or the coextruded base balloon 10, the fiber braid 20, the layer 24 and the layer 26 or any other combination thereof. The fiber braid 20 includes windows 18 within the fiber braid pattern wherein the thermoplastic polymer layer 22 of the coextruded base balloon 10 may be exposed. When the coextruded base balloon 10 includes the layer 24 and/or the layer 26, the thickness of the composite balloon 11 may have a lesser wall thickness than the portions of the composite balloon 11 where the fiber braid 20 is present as shown in the FIG. 3.

As discussed above, the coextruded base balloon 10 may be formed from a coextrusion of an elastomeric polymer material and a thermoplastic polymer. As used herein, an elastomeric polymer material may be understood to refer to polymers that are suitable for use in making expandable medical balloons, for example, elastomeric block copolymers having at least one soft block and at least one hard block, for example, block copolymers comprising at least one polyester, polyether, polyamide or polyurethane block. Suitable elastomeric polymers are discussed in more detail below. In some embodiments, the coextruded base balloon 10 is formed from a coextrusion including an inner layer 21 of a polyether-block-amide block copolymer and an outer layer 22 of a thermoplastic polyurethane. In some embodiments, the fiber braid 20 is formed from a Vectran® liquid crystal polymer (LCP) fiber, for example, an aromatic polyester LCP fiber, an ultra high molecular weight polyethylene fiber, an Aramid fiber, or combinations thereof. Materials employed to form the coextruded base balloon 10, the fiber braid 20, and any additional layers, are discussed in more detail below. The fiber braid 20 may be formed from a polymer material, for example, a polymer material that provides high strength, high modulus, and very low elongation. The thermoplastic polymer layer 22 of the coextruded base balloon 10 may be formed from a low durometer, friction-enhancing thermoplastic polymer, for example, a thermoplastic polyurethane, the fiber braid 20 may be formed from an aromatic polyester LCP fiber, the layer 24 may be formed from a thermoplastic polymer, for example, a thermoplastic polyurethane, and the outer layer 26 may be a lubricious coating layer.

Figure 4:
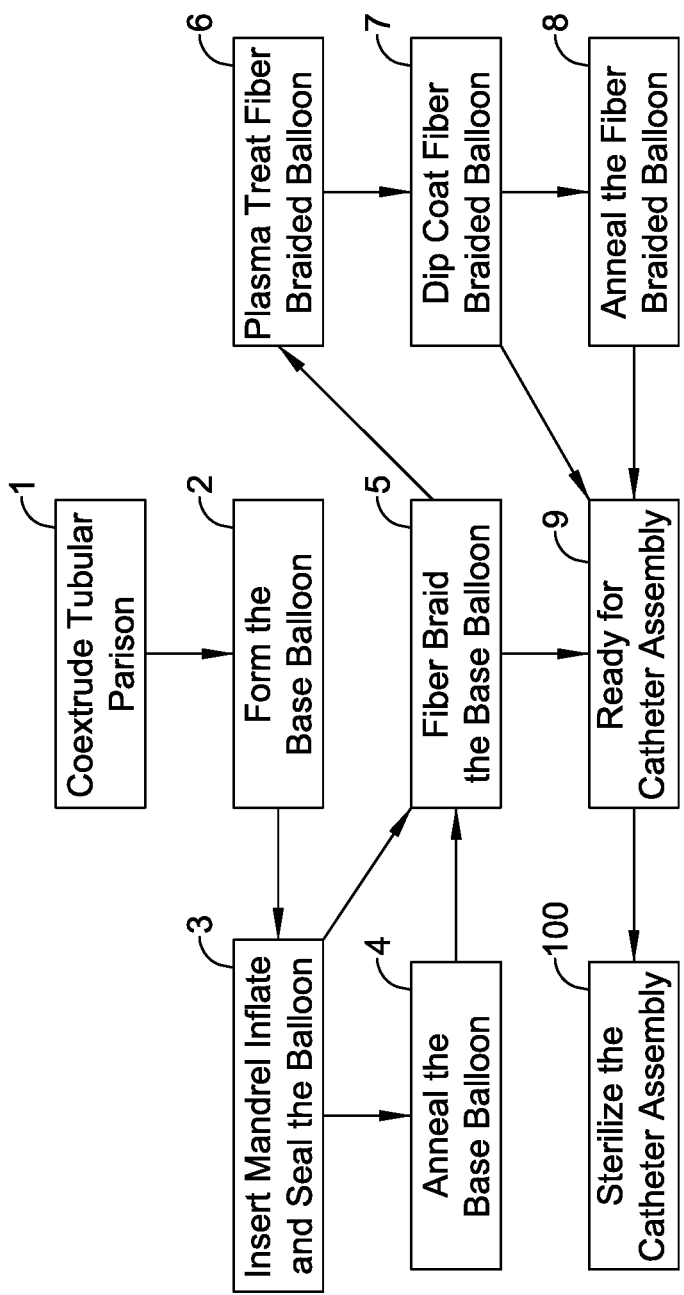
FIG. 4 is a process flow diagram illustrating an example method of forming an example medical device.

FIG. 4 is a block flow diagram illustrating an example method of making the example composite balloon 11. Generally, as illustrated at block number 1, a tubular parison of a suitable polymer materials (e.g., a coextrusion that includes the elastomeric polymer layer 21 and the thermoplastic polymer layer 22) is coextruded, and the coextruded base balloon 10 may be formed using conventional methods such as, for example, radial expansion of a tubular parison in a balloon mold as shown at block number 2. The coextruded base balloon 10 may be preformed, for instance, by radial expansion of a tubular parison, which is optionally also longitudinally stretched. The extruded parison may be radially expanded as is into a mold or by free-blowing. Alternatively, the parison may be pre-stretched longitudinally before expansion or reformed in various methods to reduce the thickness of the balloon cone and waist regions prior to radial expansion. The blowing process may utilize pressurization under tension, followed by rapid dipping into a heated fluid; a sequential dipping with differing pressurization; and a pulsed pressurization with compressible or incompressible fluid, after the material has been heated. Heating may also be accomplished by heating the pressurization fluid injected into the parison. Balloon diameters may range from 4 mm to 26 mm depending on the application, or about 4 mm to about 12 mm for some applications. In some embodiments, the tubular parison is radially expanded in a balloon mold subjected to a water bath at a temperature of less than about 100° C., for example, about 95° C. to form the coextruded base balloon 10.

The fiber braid 20 is disposed on the coextruded base balloon 10 as shown at block number 3. Again, layers 24, 26, or any additional layers may be disposed over the fiber braid 20 as well. In some embodiments, an inflated and sealed coextruded base balloon 10 may be braided with Vectran® LCP fibers, commercially available from Kuraray America Inc., using a 48 carrier Steeger USA braider. The fiber braid 20 may be disposed on the coextruded base balloon 10, for example, by braiding using 48 carriers, five filaments per carrier with each filament being 25 μm in diameter, and 12 longitudinal carriers, 20 filaments per carrier, with each filament being 25 μm in diameter. The radial fibers had a braid angle of 66 degrees to the axial direction of the balloon.

In some embodiments, the coextruded base balloon 10 may be braided with Vectran® LCP fibers, commercially available from Kuraray America Inc, using a 32 carrier Steeger USA braider. An 8×100 mm coextruded base balloon 10 may for example, be braided using 32 carriers, each with 10 individual filaments, each filament being 25 µm in diameter, and 16 longitudinal carriers composed of 15 individual filaments, each filament being 25 µm in diameter.

In some embodiments, the coextruded base balloon 10, prior to application of the fiber braid 20, may be subjected to an annealing process at an elevated temperature as shown in block 5, for example, at a temperature in the range of about 60° C. to about 80° C. In some embodiments, wherein the thermoplastic polymer layer 22 of the coextruded base balloon 10 is a thermoplastic polyurethane layer 22, the annealing is conducted at a temperature of about 70° C. The temperature of annealing is determined by the glass transition temperature ($T_g$) of the thermoplastic polymer layer 26 that is employed. The annealing temperature is not limited to the ranges disclosed herein and is determined by and set above the $T_g$ of the polymer layer employed.

In some embodiments, a mandrel is first inserted into the coextruded base balloon 10 shown at block number 4, the coextruded base balloon 10 is inflated, for example at a pressure of about 15 psi, and the proximal end of the proximal waist portion 16a and the distal end of the distal waist portion 16b are sealed prior to annealing of the coextruded base balloon 10 as shown in block number 5.

After disposing the fiber braid 20 on the coextruded base balloon 10, the now fiber-braided composite balloon 11 may also be subjected to a plasma treatment shown at block number 6, and then once again solvent dip-coated with a solution containing a thermoplastic polymer material, for example, a thermoplastic polyurethane as shown at block number 7. At this point, the composite balloon 11 may be again subjected to an annealing process at an elevated temperature as shown at block number 8, for example, in the ranges provided above. The composite balloon 11 is now ready for catheter assembly illustrated at block number 9, and the entire assembly can be sterilized as illustrated at block number 100, for example, using ethylene oxide, at an elevated temperature(s). This may involve a heat sterilization cycle, for example, wherein the catheter assembly, for example, the balloon catheter 113 shown in cross-sectional FIG. 6 and discussed below, is sterilized using a suitable material, for example, ethylene oxide, at temperatures in the range of about 40° C. to about 100° C., or about 40° C. to about 80° C. or about 40° C. to about 60° C. In some embodiments, heat sterilization is conducted at temperatures of about 47° C. to about 55° C. using ethylene oxide. The total duration of heat sterilization may range from about 5 hours to about 35 hours, or from about 10 hours to about 30 hours or from about 15 hours to about 30 hours. In some embodiments, heat sterilization is conducted from about 16 to about 27 hours.

The present disclosure is directed to a balloon design that reduces, or eliminates, the amount of delamination between the layers 21, 22 of the coextruded base balloon 10, which also reduces or minimizes delamination of the fiber braid 20 from the base balloon 10 and any subsequent layers, for example the layer 24, the layer 26, or combinations thereof, and any additional layers that may be present. Coextrusion of the elastomeric polymer layer 21 and the thermoplastic polymer layer 22 of the coextruded base balloon 10 can reduce or minimize delamination of not only the layers 21, 22, but subsequent layers as well including, for example, the fiber braid 20, and the layer 24, the layer 26, and any additional layers.

The composite balloon 11 may be capable of being inflated to relatively high pressures. For example, the composite balloon 11 may be inflated to pressures up to about 20 atm or more, or up to about 25 atm or more, or up to about 30 atm or more, or up to about 40 atm or more, or up to about 45 atm or more, or up to about 50 atm or more, or about 20-50 atm, or about 25-40 atm, or about 30-50 atm. Furthermore, the bond between the layers 21, 22 of the coextruded base balloon 10, and between the fiber braid 20 and the coextruded base balloon 10 is also maintained at these elevated pressures reducing or minimizing delamination between the fiber braid 20 and the coextruded base balloon 10.

As indicated herein, the coextruded base balloon 10 may be formed from a coextrusion of an elastomeric polymer (e.g., such as a poly(ether-block-amide) copolymer) and a thermoplastic polyurethane (TPU), for example, Pellethane® 2363-75D thermoplastic polyurethane, which is commercially available from Lubrizol Advanced Materials in Cleveland, Ohio, Avalon® or Irogran® TPUs available from Huntsman Corp. in The Woodlands, Tex., Elastollan® TPUs available from BASF Polyurethanes North America located in Wyandotte, Mich., and so forth. The polyamide/polyether block copolymers are commonly identified by the acronym PEBA (polyether block amide). The polyamide and polyether segments of these block copolymers may be linked through amide linkages, for example, some are ester linked segmented polymers, e.g., polyamide/polyether polyesters. Such polyamide/polyether/polyester block copolymers are made by a molten state polycondensation reaction of a dicarboxylic polyamide and a polyether diol. The result is a short chain polyester made up of blocks of polyamide and polyether. Polymers of this type are commercially available under the tradename of Pebax® from Arkema. Specific examples are the "33" series polymers with hardness 60 and above, Shore D scale, for example, Pebax® 6333, 7033 and 7233. These polymers are made up of nylon 12 segments and poly(tetramethylene ether) segments linked by ester groups.

Polyester/polyether segmented block copolymers may also be employed herein. Such polymers are made up of at least two polyester and at least two polyether segments. The polyether segments are the same as previously described for the polyamide/polyether block copolymers useful in the disclosure. The polyester segments are polyesters of an aromatic dicarboxylic acid and a two to four carbon diol.

In some embodiments, the polyether segments of the polyester/polyether segmented block copolymers are aliphatic polyethers having at least 2 and no more than 10 linear saturated aliphatic carbon atoms between ether linkages. The ether segments may have 4-6 carbons between ether linkages, and they may include poly(tetramethylene ether) segments. Examples of other polyethers which may be employed in place of the tetramethylene ether segments include polyethylene glycol, polypropylene glycol, poly(pentamethylene ether) and poly(hexamethylene ether). The hydrocarbon portions of the polyether may be optionally branched. An example is the polyether of 2-ethylhexane diol. Generally, such branches will contain no more than two carbon atoms. The molecular weight of the polyether segments is suitably between about 400 and 2,500, and more suitably between 650 and 1000.

In some embodiments, the polyester segments of the polyester/polyether segmented block copolymers are polyesters of an aromatic dicarboxylic acid and a two to four carbon diol. Suitable dicarboxylic acids used to prepare the polyester segments of the polyester/polyether block copolymers are ortho-, meta- or para-phthalic acid, napthalenedicarboxylic acid or meta-terphenyl-4,4'-dicarboxylic acids. Specific examples of polyester/polyether block copolymers are poly(butylene terephthalate)-block-poly(tetramethylene oxide) polymers such as Arnitel® EM 740, sold by DSM Engineering Plastics, and Hytrel® polymers, sold by DuPont, such as Hytrel® 8130.

The fiber braid 20 may be formed from a variety of suitable materials. Some specific examples include, but are not limited to, polyesters such as polyethylene terephthalate (PET), polybutylene terephthalate (PBT), and polytrimethylene terephthalate (PTT). Polyamides include nylons and aramids such as Kevlar®. Polyolefins include ultra high molecular weight polyethylene, and very high density polyethylene, and polypropylene fibers. Combinations of fibers are also contemplated. In some specific embodiments of the disclosure, fibers that are high strength materials may also be suitable in some applications.

In some embodiments, the fiber braid 20 is formed using a high melting temperature fiber, for example, a liquid crystal polymer, for example, Vectran®, an aromatic polyester available from Kuraray Ltd., USA, and having their headquarters located in Tokyo, Japan. In some embodiments, the liquid crystal polymer is formed by the polycondensation of 4-hydroxybenzoic acid and 6-hydroxynaphthalene-2-carboxylic acid.

The fiber braid 20 may also be formed from an ultra high molecular weight polyethylene (UHMPE). Commercially available UHMPEs include, but are not limited to, Dyneema® fiber available from DSM Dyneema BVm Heerlen, Netherlands, Spectra® fiber available from Honeywell in Morristown and Pegasus UHMWPE fiber available from Pegasus Materials in Shanghai, China.

The fiber braid 20 may also be formed from a copolyamide, for example, Aramid fiber. Aramid fiber are aromatic polyamides and can be classified as heat-resistant, non-melting fibers wherein degradation starts from 500° C. Typically, aramids are long-chain polyamides wherein at least 85% of the amide linkages are attached to two aromatic rings. Many of these materials are classified as having no melting point. One commercially available aramid fiber is Technora®, para-aramid which is a polyamide copolymer. Technora® fiber is available from Teijin Aramid, a subsidiary of the Teijin Group in the United Kingdom. Other examples of suitable aramid fibers include, but are not limited to, Kevlar® fiber available from DuPont in Wilmington, Del., Nomex® meta-aramid fiber also available from DuPont, and Twaron fiber which is also available from Teijin Aramid.

Figure 5:
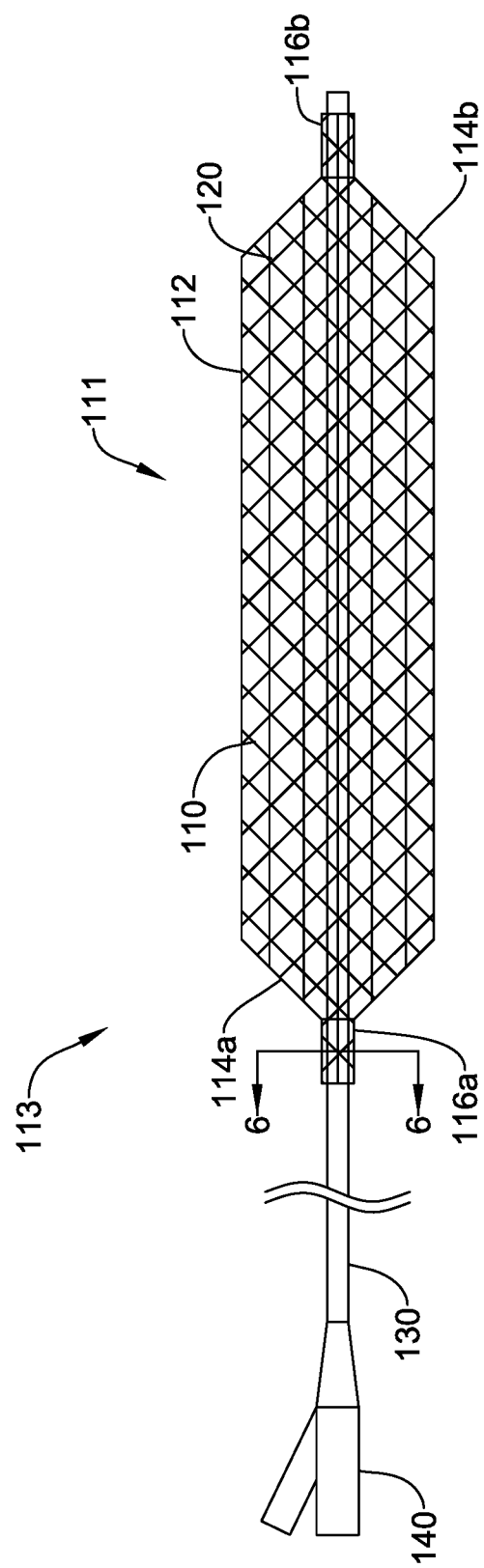
FIG. 5 is a side view of an example medical device.

A side view of an exemplary balloon catheter 113 is illustrated in FIG. 5 with a composite balloon 111 assembled on the balloon catheter 113. The composite balloon 111 may be mounted on the distal end of a catheter shaft 130. The composite balloon 111 may be the same as or similar to the composite balloon 11, as shown and described with reference to FIGS. 3-5 and may include a coextruded base balloon 110 (similar in form and function to the coextruded base balloon 10). A fiber braid 120 may be disposed along the outer surface of the coextruded base balloon 110. Catheter shaft 130 extends from a manifold assembly 140 at a proximal end of the catheter shaft 130. The composite balloon 111 is shown having a body portion 112, a proximal cone portion 114a, a distal cone portion 114b, a proximal waist portion 116a, and a distal waist portion 116b. The composite balloon 111 may be secured to the catheter shaft 130 at the proximal waist portion 116a and the distal waist portions 116b, respectively.

Figure 6:
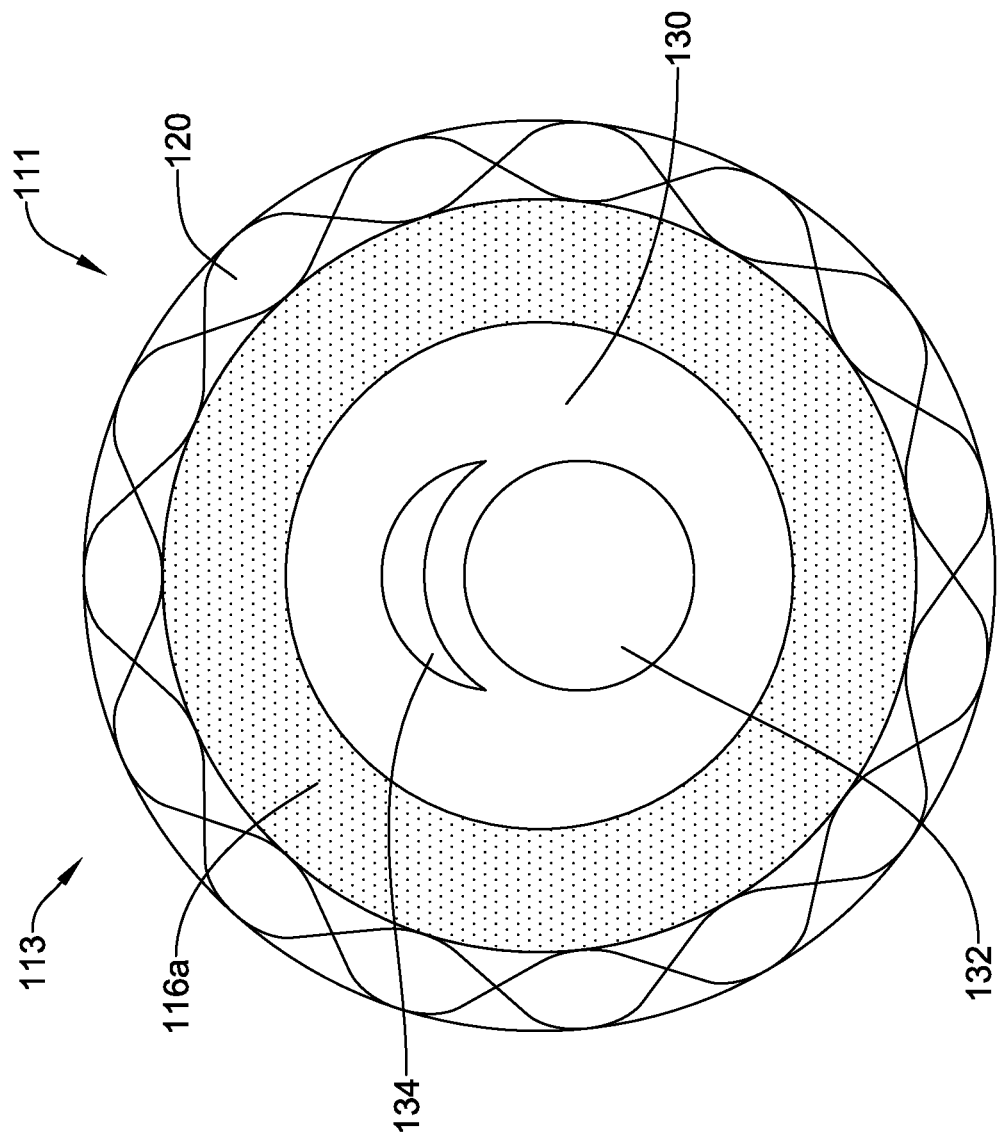
FIG. 6 is a cross-section of an example medical device taken at section 6-6 in FIG. 5.

FIG. 6 is a cross-sectional view of the balloon catheter 113 taken at section 6-6 of FIG. 5. The catheter shaft 130 is depicted as a dual-lumen catheter shaft 130 that includes a guidewire lumen 132 for a guidewire and an inflation lumen 134 for inflation of the composite balloon 111. Alternatively, the catheter shaft 130 may include an inner tubular member defining the guidewire lumen 132 and an outer tubular member extending around the inner tubular member. In these instances, the inflation lumen 134 may be defined between the inner tubular member and the outer tubular member. In such cases, the proximal waist portion 116a may be secured to a distal end region of the outer tubular member and the distal waist portion 116b may be secured to a distal end region of the inner tubular member. Other catheter shafts are contemplated.

The composite balloon 111 may be capable of being inflated to relatively high pressures. For example, the composite balloon 111 may be inflated to pressures up to about 20 atm or more, or up to about 25 atm or more, or up to about 30 atm or more, or up to about 40 atm or more, or up to about 45 atm or more, or up to about 50 atm or more, or about 20-50 atm, or about 25-40 atm, or about 30-50 atm. At such elevated pressures, the bond between the proximal waist portion 116a and the catheter shaft 130, as well as the bond between the distal waist portion 116b and the catheter shaft 130 is maintained. Furthermore, the bond between the fiber braid 120 and the coextruded base balloon 110 is also maintained at these elevated pressures reducing or minimizing delamination between the fiber braid 120 and the coextruded base balloon 110.

The catheter shaft 130 may be formed from any suitable shaft material. Examples include, but are not limited to, polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the catheter shaft 130 can be formed by also blending a polymer material a liquid crystal polymer (LCP). For example, the shaft material mixture can contain up to about 6 percent LCP. In some embodiments, the catheter shaft 230 is formed from a polyamide, for example Grilamid® which is commercially available from EMS-Grivory.

The above lists are intended for illustrative purposes only, and not as a limitation on the present disclosure. It is within purview of those of ordinary skill in the art to select other polymers without departing from the scope of this disclosure.

EXAMPLES

Example 1

A tubular parison having an outer diameter (OD) of 0.0688" (1.75 mm) and an inner diameter (ID) of 0.0525" (1.33 mm) was coextruded with an inner layer of Pebax® 7033 polyether-block-amide copolymer having a thickness of 0.002" (0.05 mm), and an outer layer of Pellethane® 2363-75D thermoplastic polyurethane having a thickness of 0.0062" (0.16 mm). The length of the tubular parison was 100 mm.

The coextruded tubular parison was stretched under pressure in a 45 C hot bath and then placed in a balloon mold and radially expanded while the balloon mold was in a water bath at 95° C. to form the coextruded base balloon having a coextrusion of an inner layer of Pebax® 7033 and an outer layer of Pellethane® 2363-75D.

The coextruded base balloons were compared to base balloons that were formed by extruding a monolayer of Pebax® 7033 to form the tubular parison followed by dipping the tubular parison in a mixture of 2.5% solids, Lubrizol Tecoflex SG60D in a cosolvent blend of 50% toluene/50% tetrahydrofuran. The dipping process may be repeated up to three times to achieve the desired thickness with 1 minute in between each cycle, at a dip down and up speed of 50 inches/minute, with a hold time of 2 seconds in a 100 ml graduated cylinder.

A sampling of each set of base balloons (extruded and dipped versus coextruded) was then subjected to various plasma treatment cycles as shown in Table 1. Prior to plasma treatment, a stainless steel mandrel was inserted into each base balloon, and the base balloons were then inflated to 15 psi and the proximal and distal ends of the base balloon are sealed.

TABLE 1

| Recipe | Gas | Power (W) | Time (sec) | Gas Flow (sccm) | Number of cycles | Notes |
|---|---|---|---|---|---|---|
| | N/A | N/A | N/A | N/A | N/A | No plasma |
| 1 | Oxygen | 125 | 90 | 100 | 1 | Horizontal |
| 2 | Oxygen | 250 | 180 | 100 | 1 | Horizontal |
| 3 | Oxygen | 250 | 90 | 100 | 4 | Vertical 1 flip, 3 rotations |
| 4 | Oxygen | 500 | 60 | 1000 | 1 | Horizontal |

The reference to horizontal and vertical refers to how each of the base balloons were orientated in the plasma chamber. For those base balloons that were vertically orientated, the balloons were flipped once, and then rotated three times for placement of the base balloons in each corner of the plasma chamber during the treatment cycle.

The shear force was measured and the base balloons were compared to base balloons having no plasma treatment. For shear force testing, the base balloons were deflated, flattened, and cut in half in the radial direction. A pipette was then used to place a 5 μL drop of 2.5% Lubrizol SG 60D thermoplastic polyurethane in 50% Toluene/50% THF and onto the center of trailing end of balloon ~0.25" from the cut edge. It was ensured that each base balloon was flat and smooth before placing the drop.

The leading half of the base balloon was then placed over the trailing half so that each half of the balloon was "glued" together with an overlap of ~0.5". It was ensured that the surface of the leading half of the balloon was smooth and flattened before putting the two halves together, and that each half of the base balloon was parallel to each other. Little time was allowed to lapse between drop placement and covering of the two halves, to ensure that the thermoplastic polyurethane solution did not begin to dry, and it was confirmed that no thermoplastic polyurethane solution was leaking around the edges of the overlapping halves of the base balloon.

A weight of approximately 4.7 g was placed on the overlapping portion of the base balloon halves. The samples were allowed to dry overnight. The samples were then soaked in a 37° water bath for at least an hour prior to testing.

The samples were then removed from the water bath and placed in the tensile tester clamps with the leading edge of each sample facing up. Gage length was set so that the clamps grab onto balloon waist just past the cone/waist transition. For example, for a 12 mm×60 mm balloon, the gage length was 70 mm. Tensile testing was conducted at a speed of 7 inches/minute.

Figure 7:
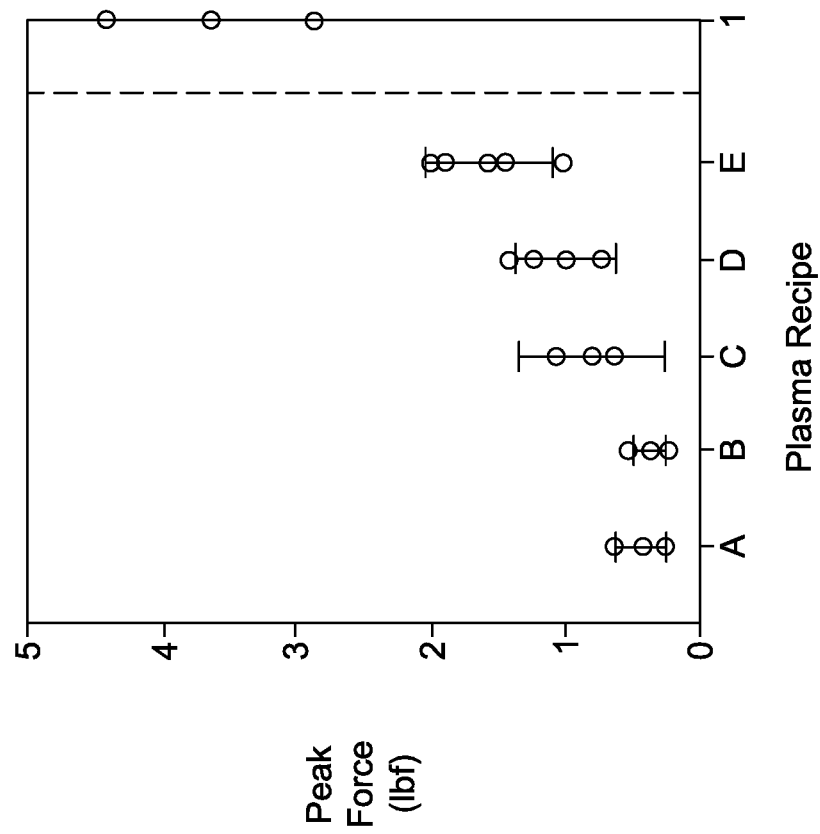
FIG. 7 is a graph illustrating the impact of plasma treatment on the shear strength of an example medical balloon.

FIG. 7 is a graph illustrating the results of shear force of base balloons that were extruded, and plasma treated versus base balloons that were coextruded, without plasma treatment. The sample set, labeled as 1 in the graph had no plasma treatment and some of the samples were treated with a variety of different plasma recipes as shown in Table 1.

As can be seen from FIG. 7, the extruded base balloons, comparative samples A (no plasma treatment), B (plasma recipe 1), C (plasma recipe 2), D (plasma recipe 3), and E (plasma recipe 4), exhibited significantly lower shear force values than the coextruded base balloons, sample set 1, having no plasma treatment.

Example 2

A tubular parison having an outer diameter (OD) of 0.0688" (1.75 mm) and an inner diameter (ID) of 0.0525" (1.33 mm) was coextruded with an inner layer of Pebax® 7033 polyether-block-amide copolymer having a thickness of 0.002" (0.05 mm), and an outer layer of Pellethane® 2363-75D thermoplastic polyurethane having a thickness of 0.0062" (0.16 mm). The length of the tubular parison was 100 mm.

The coextruded tubular parison was stretched with pressure at 45 C and placed in a balloon mold and radially expanded while the balloon mold was in a water bath at 95° C. to form the coextruded base balloon having an inner layer of Pebax® 7033 and an outer layer of Pellethane® 2363-75D.

A stainless steel mandrel was inserted into each coextruded base balloon, and the coextruded base balloons were then inflated to 15 psi and the proximal and distal ends of the coextruded base balloons were sealed.

The coextruded base balloon was then braided with Vectran® LCP fibers, commercially available from Kuraray, using a 48 carrier Steeger braider. An 8×100 mm coextruded base balloon was braided using 48 carriers, five filaments per carrier with each filament being 25 μm in diameter, and 12 longitudinal carriers, 20 filaments per carrier, with each filament being 25 μm in diameter. The radial fibers had a braid angle of 66 degrees to the axis of the balloon.

The composite balloons were separated into three groups. Some of the composite balloon samples were treated with a first plasma recipe which included a plasma cycle of 100 sccm $O_2$, 250 W, 300 sec, with horizontal composite balloon orientation in the plasma chamber, and with one continuous cycle.

Some of the composite balloon samples were treated with a second plasma recipe, which included a plasma cycle of 100 sccm $O_2$, 250 W, 300 sec, the balloon having a horizontal composite balloon orientation in the plasma chamber, and treated with one continuous cycle.

Some of the composite balloon samples were treated with a third plasma recipe, that included a plasma cycle of 200 sccm Ar, 100 sccm O2, 450 W, 120 sec, the balloon having a horizontal composite balloon orientation in the plasma chamber, and treated with one continuous cycle.

Figure 8:
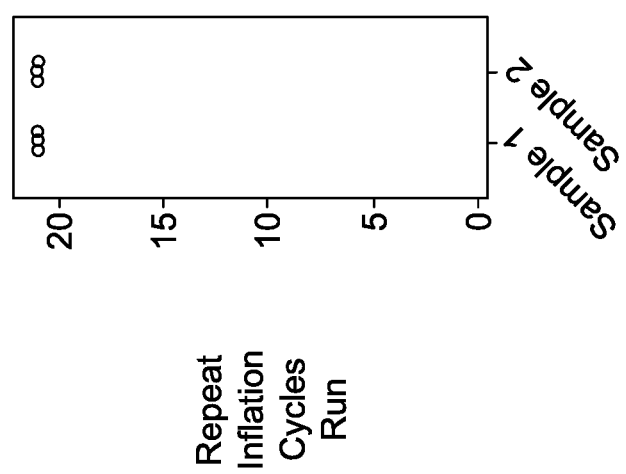
FIG. 8 is a graph illustrating the effect of repeat inflation cycles on the delamination of an example medical balloon.

FIG. 8 is a graph illustrating the effect on the occurrence of delamination of balloon samples treated with plasma recipe 1 (labeled in the graph as sample 1) and with plasma recipe 2 (labeled in the graph as sample 2) upon repeat catheter inflation bench testing at a rated burst pressure of the composite balloons.

Delamination was determined by running repeat inflation cycles on an 8×100 mm coextruded base balloon. The coextruded base balloon was inflated at a rate of 1.36 atmosphere/second (20 psi/sec) in a 37° C. water bath to a rated burst pressure of 30 atmospheres (440 psi) and held for 30 seconds, and then deflated and evacuated to a pressure of 0.3 atmospheres (4.4 psi) and held for 15-20 seconds, visually inspected, and the cycle repeated, in up to, or more than, 20 cycles.

After each cycle, the coextruded base balloons were visually inspected for delamination, fiber movement, cone rounding, or burst. The coextruded base balloons were then returned to the water bath and the cycle was repeated. The total time at vacuum between cycles was 45 seconds, including the observation time.

The composite balloons in each group were inflated to the rated burst pressure from one to twenty cycles. The composite balloons that were treated with plasma recipe 1 (labeled in the graph as sample 1) and with plasma recipe 2 (labeled in the graph as sample 2) exhibited no delamination after 20 repeat inflation cycles, and the test was then stopped. The empty circles in the graph represent that no delamination was observed in the individual composite balloons tested for each of sample 1 (plasma recipe 1) and sample 2 (plasma recipe 2).

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A composite expandable medical balloon, comprising:
   a base balloon comprising a coextrusion, the coextrusion comprising an inner layer formed from an elastomeric polymer, the inner layer comprises a polyether-block-amide, and an outer layer formed from a thermoplastic polymer, the outer layer comprises a thermoplastic polyurethane; and
   a fiber braid disposed on and in direct contact with the thermoplastic polymer layer of the base balloon, the fiber braid comprising at least one polymeric fiber disposed over the base balloon;
   wherein the base balloon is designed to exhibit minimal delamination between the inner layer and the outer layer of the base balloon.

2. The composite expandable medical balloon of claim 1, wherein the at least one polymeric fiber comprises an aromatic polyester liquid crystal polymer fiber.

3. The composite expandable medical balloon of claim 1, wherein the at least one polymeric fiber comprises an aromatic polyamide copolymer fiber.

4. The composite expandable medical balloon of claim 1, wherein the at least one polymeric fiber comprises an ultra high molecular weight polyethylene fiber.

5. The composite expandable medical balloon claim 1, wherein the composite expandable medical balloon further comprises at least one first layer disposed on the fiber braid, the at least one first layer comprising a thermoplastic polymer.

6. The composite expandable medical balloon of claim 5, wherein the at least one first layer comprises a thermoplastic polyurethane.

7. The composite expandable medical balloon of claim 5, further comprising at least one second layer, the at least one second layer comprising a lubricious material, the at least one second layer being an outermost layer.

8. A composite expandable medical balloon, comprising:
   a base balloon formed from a coextrusion comprising an inner layer of an elastomeric polymer, and an outer layer of a thermoplastic polyurethane; and
   a fiber braid comprising at least one polymeric fiber disposed on and in direct contact with the outer layer of the base balloon;
   wherein the base balloon is designed to exhibit minimal delamination between the inner layer the outer layer of the base balloon;
   wherein the composite expandable medical balloon exhibits a rated burst strength of between about 30-70 atmospheres.

9. The composite expandable medical balloon of claim 8, wherein the elastomeric polymer is a polyether-block-amide copolymer.

10. The composite expandable medical balloon of claim 8, further comprising at least one first layer disposed over the fiber braid, the at least one first layer comprising a thermoplastic polymer.

11. The composite expandable medical balloon of claim 10, wherein the first layer comprises a thermoplastic polyurethane.

12. The composite expandable medical balloon of claim 8, wherein the fiber braid comprises an aromatic liquid crystal polymer.

13. A method of forming a composite expandable medical balloon, the method comprising:
   coextruding a tubular member, the tubular member comprising an inner layer of an elastomeric polymer, the elastomeric polymer is a polyether-block amide, and an outer layer of a thermoplastic polymer, the thermoplastic polymer is a polyurethane;

radially expanding the tubular member to form a base balloon; and disposing a fiber braid comprising at least one polymeric fiber along the base balloon to form a composite balloon;

wherein the base balloon is designed to exhibit minimal delamination between the inner layer and the outer layer of the base balloon.

14. The method of claim 13, further comprising plasma treating the composite balloon after disposing the fiber braid along the base balloon.

15. The method of claim 13, further comprising disposing a first layer over the fiber braid, the first layer comprising a thermoplastic polymer.

16. The method of claim 13, wherein the at least one polymeric fiber is an aromatic polyester liquid crystal polymer fiber.

17. The composite expandable medical balloon of claim 1, the fiber braid comprising radial fibers having a braid angle of 68 degrees to an axial direction of the balloon.

18. The composite expandable medical balloon of claim 1, wherein the composite expandable medical balloon exhibits a rated burst strength of between about 30-70 atmospheres.

19. The method of claim 13, wherein the fiber braid comprises radial fibers having a braid angle of 68 degrees to an axial direction of the balloon.

20. The method of claim 13, wherein the resultant composite expandable medical balloon exhibits a rated burst strength of between about 30-70 atmospheres.

* * * * *